United States Patent
Allen et al.

[11] Patent Number: 5,843,068
[45] Date of Patent: Dec. 1, 1998

[54] DISPOSABLE DIAPER HAVING ELASTIC SIDE PANELS

[75] Inventors: Martin A. Allen; John T. Fetcko, both of Dawsonville, Ga.

[73] Assignee: J&M Laboratories, Inc., Dawsonville, Ga.

[21] Appl. No.: 928,260

[22] Filed: Sep. 12, 1997

Related U.S. Application Data

[63] Continuation of Ser. No. 492,745, Jun. 21, 1995, abandoned.

[51] Int. Cl.$^6$ ............................................. A61F 13/15
[52] U.S. Cl. ........................ 604/385.2; 604/392; 604/396; 604/387
[58] Field of Search .................. 604/378, 385.1, 604/385.2, 386, 387, 392–394, 396

[56] References Cited

U.S. PATENT DOCUMENTS

| | | | |
|---|---|---|---|
| Re. 28,688 | 1/1976 | Cook | 260/4 |
| 4,205,679 | 6/1980 | Repke et al. | 604/394 |
| 4,646,362 | 3/1987 | Heran et al. | 604/385.2 |
| 4,808,252 | 2/1989 | Lash | 604/385.2 |
| 4,891,258 | 1/1990 | Fahrenkrug | 604/385.2 |
| 4,938,757 | 7/1990 | Van Gompel et al. | 604/385.2 |
| 5,226,992 | 7/1993 | Morman | 156/62.4 |
| 5,236,430 | 8/1993 | Bridges | 604/393 |
| 5,244,482 | 9/1993 | Hassenboehler | 55/528 |
| 5,470,639 | 11/1995 | Gessner et al. | 604/385.2 |

*Primary Examiner*—Mark O. Polutta
*Attorney, Agent, or Firm*—R. L. Graham

[57] ABSTRACT

A form fitting diaper comprises a backsheet having a front section, a back section, and a crotch section, and has bonded thereto an absorbent layer. The diaper further comprises a pair of elastic side panels bonded between the front and back sections of the backsheet and define therewith a circumferentially continuous and elastic waist, and further defining leg openings. The side panels having substantially unidirectional elasticity whereby the panels are elastic in the circumferential direction and substantially inelastic in the direction perpendicular thereto. The side panels being of composite construction comprising an elastomeric layer with a unidirectionally elastic nonwoven layer bonded thereto. The composite combines the barrier and strength properties of the elastomeric layer with the unidirectional elasticity and fabric-like properties of the nonwoven layer. The unidirectional elasticity of the composite is useful for putting on and taking off the diaper. The elastic nonwoven layer being formed by heat drawing substantially nonelastic meltblown or spunbond fibers.

13 Claims, 4 Drawing Sheets

DISPOSABLE DIAPER HAVING ELASTIC SIDE PANELS

RELATED APPLICATION

This is a continuation of U.S. application Ser. No. 08/492,745, filed Jun. 21, 1995, now abandoned.

BACKGROUND OF THE INVENTION

This invention relates generally to form fitting diapers or garments containing elastic panels. In one aspect, the invention relates to a diaper containing an elastic panel of a composite comprising (a) an elastomeric layer and (b) an elastic nonwoven web composed of nonelastic fibers.

Modern diapers must possess many qualities: they must be disposable, comfortable, form fitting, and have a pleasing appearance and feel (e.g. hand). The form fitting requirement has led to the use of elastic panels in diapers. Examples include elastic strips in the waist band and leg. A recent use of elastic panels are side panels used in "pull-up" or "training" diapers.

U.S. Pat. No. 4,938,753 discloses a training diaper provided with elastic side panels. The side panels comprise an elastomeric layer flanked by nonelastic nonwovens.

An article entitled "Stretchable Fabric Technology Options", *Nonwovens World,* Spring 1994 (pages 49–56), describes various elastic fabrics for use in disposable products.

Thermoplastic elastomers have been used in many applications, and while they possess the necessary elastic properties, they have a rubbery or plastic appearance and/or hand. Nonwovens are widely used in disposable products. These materials have a cloth-like appearance and are comfortable, but are generally inelastic and therefore are not form fitting.

Efforts to combine nonwovens and elastomerics are disclosed in U.S. Pat. Nos. 4,720,415; 4,652,487; and 4,657,802. These Patents disclose processes wherein the elastomeric film is stretched and thermally or adhesively bonded to an elastomeric web whereby, upon release of the tension, the elastomeric web contracts and the inelastic web gathers or ruffles between the bond areas.

Recent developments in "stretchable" nonwovens of the type disclosed in U.S. Pat. No. 5,244,482 exhibit some elasticity, but not enough for many applications. Moreover, these fabrics do not exhibit sufficient "elongation-at-break". This patent discloses that the stretchable nonwoven web may be used in combination with other webs or substrates such as webs from elastomeric polymers without specifying any end-use products for these composites.

U.S. Pat. No. 5,244,482 also discloses the heat stretching of composites (e.g. spunbond PP/meltblown PP/spunbond PP) composed of inelastic fibers (PP) to impart unidirectional elasticity thereto.

U.S. Pat. No. 5,226,992 discloses a method for forming a composite of an inelastic web and an elastic sheet. In this process an inelastic web is stretched in one direction to cause the web to neck down in the direction perpendicular to stretch. An elastomeric sheet is then bonded to the fabric while it is in the necked position. Upon release of the tension on the necked fabric, it assumes the dimensions of the elastomeric sheet. Stretching the elastomeric sheet in the direction of necking (perpendicular to the direction of stretch) permits the nonelastic fabric to stretch in that direction to its original size. It can be seen that the methods of U.S. Pat. No. 5,226,992 have certain disadvantages. The necked-down fabric with an elastomeric sheet is difficult to manufacture because of the need to bond the elastomeric sheet to the fabric under stressed or stretched conditions.

U.S. Pat. No. 5,306,545 discloses a meltblown nonwoven fabric formed by meltblowing an ethylene and olefin copolymer. The density and crystallinity of the copolymer are controlled so as to optimize the elasticity of the fabric. The resulting fabric exhibits elasticity in both the lateral and vertical directions. The degree of elasticity is relatively small (e.g. 10%) and the fabric exhibits some residual elongation when stretched. The aforementioned U.S. Patent discloses that the copolymer may be used in blends (such as with PP) for improved softness. The Patent further teaches that the elastic fabric may be layered with other fabrics to form laminates, which may be useful in medical applications such as flexible bandages.

SUMMARY OF THE INVENTION

The form-fitting diaper of the present invention comprises a diaper backsheet having a front section and a back section, an absorbent material positioned on an internal surface of the backsheet, and elastic side panels interconnecting the front and back sections of the backsheet. Each elastic side panel is a composite which includes dissimilar layers that are bonded together.

Briefly, each composite elastic side panel is a two-layer or three-layer composite comprising:

(a) an elastomeric layer, preferably an elastomeric film; and (b) at least one layer (in the two-layer composite) or two layers (in the three-layer composite) of an elastic nonwoven web bonded to the elastomeric layer.

Preferably, the composite comprises two layers of an elastic nonwoven web bonded to opposite sides of the elastomeric layer. In both embodiments the elastic nonwoven web is composed of nonelastic thermoplastic fibers and possesses unidirectional elasticity.

The preferred three-layer side panel comprises a core elastomeric layer bonded between two elastic nonwoven layers. The composite possesses cloth-like appearance and hand and yet exhibits unidirectional elasticity. These two properties make the composite ideal for form-fitting diapers.

As discussed in more detail below, the elastic nonwoven useful in the side panels is made by thermo-mechanically processing a normally nonelastic nonwoven web to impart unidirectional elasticity thereto.

Although the elastic composite can be made by a variety of processes, the preferred process involves the steps of:

(a) passing two of the layers under a hot melt dispenser to apply an adhesive to one side thereof; and (b) bringing the coated two layers into contact with the third layer in the nip of counter-rotating pressure rolls whereby they are pressure bonded together.

In a preferred embodiment, the elastomeric layer is made of a thermoplastic elastomer (e.g. elastomeric film), and the nonwoven layers are of meltblown polyolefin. The film imparts strong elasticity to the composite, and the meltblown polyolefin imparts unidirectional elasticity as well as a pleasing hand and appearance to the composite. In use, the inner nonwoven polyolefin layer of the diaper side panels will be in contact with the skin of the wearer. Because the meltblown polyolefin is porous, it provides a good degree of breatheability for added comfort to the wearer.

When made in accordance with the process described herein, the side panel composite will have elasticity in the cross-direction, but not the machine direction. The unidirectional stretch of the composite is an advantageous feature for the side panels in "pull up" diapers. The composite is bonded to the front and back sections of the backsheet to permit the joined sections to be stretched apart (circumferentially) during fitting (e.g. pull up). The panels, however, are not stretchable in a direction normal to the circumference of the diaper so that the wearer of the diaper can pull the diaper up (without stretch) by gripping the side panels and pulling vertically.

The three-layer composite is preferred over the two-layer composite because the nonwoven layers are either in contact with the body or exposed, giving the diaper comfort and a pleasing cloth-like appearance. However, in certain applications the two-layer composite will suffice. Both the two-layer composite and the three-layer composite exhibit the stretchability properties necessary for use in the diaper of the present invention.

DESCRIPTION OF THE PREFERRED EMBODIMENTS

Figure 1:
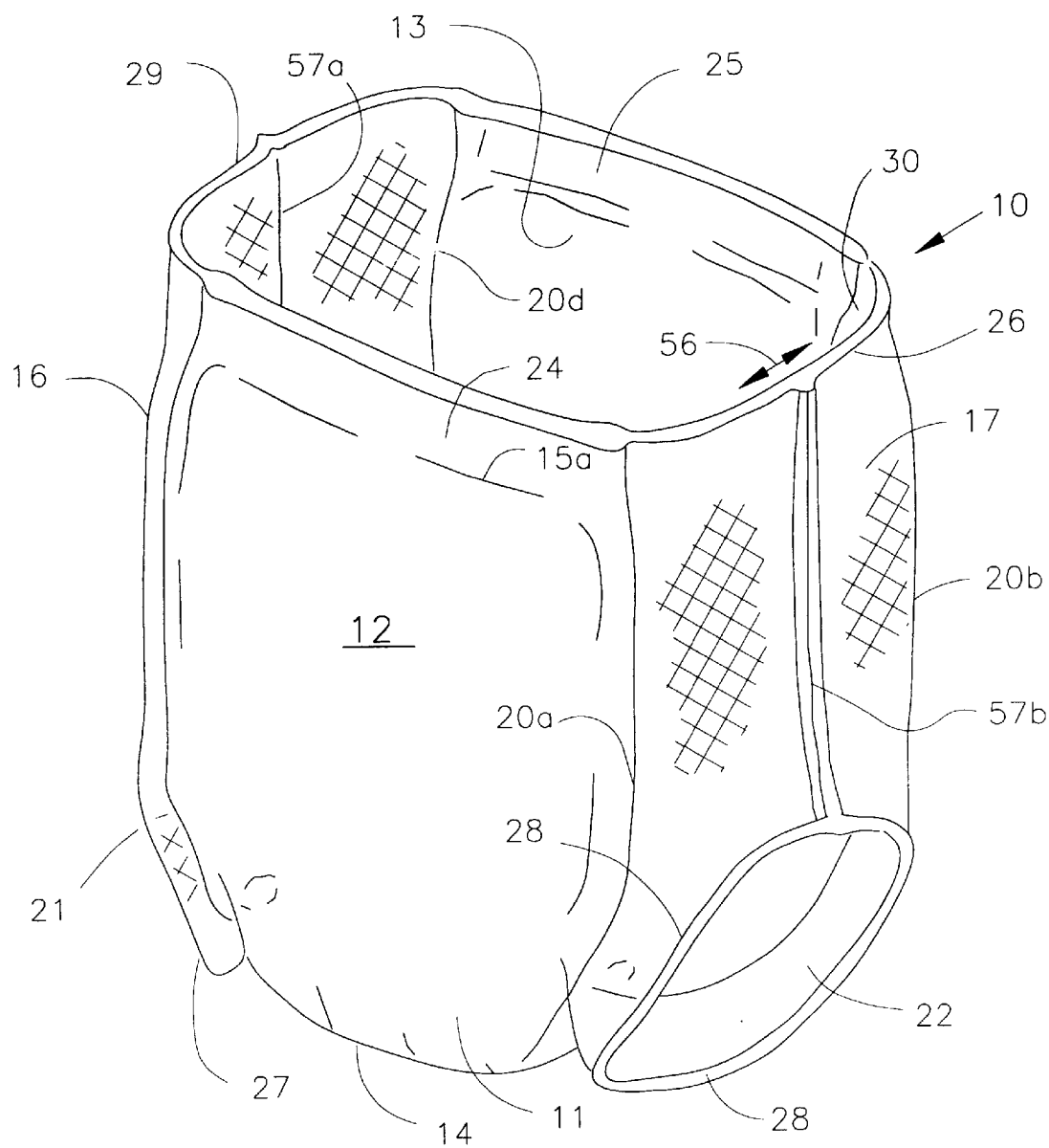
FIG. 1 is a perspective view of a form fitting diaper constructed according to the present invention.

In order to fully appreciate the present invention, it is necessary to understand certain terms used in this specialized art. Accordingly, terms used to characterize certain features of the present invention are defined below.

Definitions

The term "elasticity" refers to material capable of recovering its original shape partially (at least 40%) or completely after the deforming force has been removed.

The term "elastic" means a material which exhibits elasticity and includes elastomers and fabrics of inelastic fibers in which the fabric has been processed to impart elasticity thereto.

The term "elastomers" means elastomeric polymers that have the ability to be stretched to at least twice their original length and to retract very rapidly to approximately their original length when released. Elastomeric polymers include the synthetic thermosetting and thermoplastic polymers which have properties similar to those of vulcanized rubber such as styrene butadiene copolymer, polychloroprene (neoprene), nitrile rubber, butyl rubber, polysulfide rubber, cis-14-polyisoprene, polybutadiene, ethylenepropylene terpolymers (EPDM), silicone rubber, polyurethane rubber, polyamide elastomers, EVA and EMA elastomers, and the styrene triblock copolymers.

The preferred elastomers for use in the present invention are the styrene triblock copolymers such as styrene-butadiene-styrene block copolymer (SBS), styrene-isoprene-styrene block copolymer (SIS), and styrene-hydrogenated butadiene-styrene block copolymer (SEBS).

The terms "fibers" and "filaments" as used herein are interchangeable to mean a solid having an extremely high ratio of length to diameter. Thermoplastic fibers and filaments are made by extruding the thermoplastic from a spinneret, typically by spunbond or meltblowing processes. These processes are well known to those skilled in the art and are described in U.S. Pat. No. 5,244,482, the disclosure of which is incorporated herein by reference.

The term "nonwovens" means fabrics made from thermoplastic fibers mechanically positioned in a random manner to form a layer or sheet, and include spunbond fabrics, meltblown fabrics, carded fibers, and spunlaced. These fabrics are often referred to as nonwoven webs. The fibers used in the nonwovens are microsized ranging from 0.5 to 50 microns depending on the intended use of the web.

The term "inelastic fibers" or "nonelastic fibers" means fibers which when stretched along their length do not exhibit elasticity.

The term "inelastic nonwoven web" or "nonelastic nonwoven web" means that the nonwoven web does not exhibit elasticity.

The term "elastic recovery" means the percentage to which a specimen recovers its original length measured immediately following a given percent elongation. For example, a recovery of 90% indicates that the material will be 10% longer following the application and removal of a deforming force.

The term "draw ratio" refers to stretch (from original shape) imposed on a material in a given direction.

Form Fitting Diaper Construction

Figure 2:
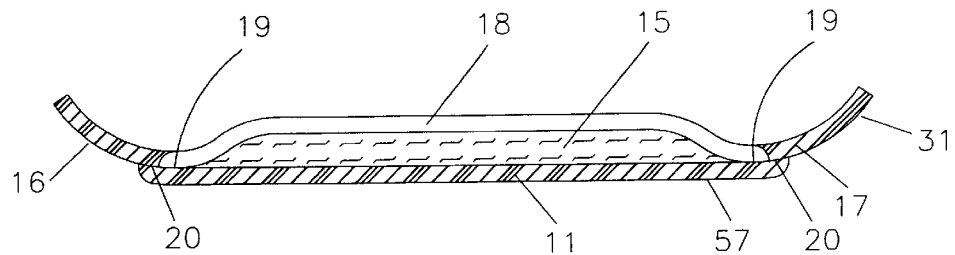
FIG. 2 is a cross-section of the front panel of the diaper shown in FIG. 1.

As shown in FIGS. 1 and 2, a diaper 10 constructed according to the present invention is in the form of a ready-to-wear body garment comprises a backsheet 11 having a front section 12, a back section 13, a crotch section 14 interconnecting sections 12 and 13, an absorbent layer 15, and elastic side panels 16 and 17. Elastic side panels 16 and 17 are bonded to the lateral edges of front section 12 and back section 13 as at 20a and 20b for panel 17, and 20c and 20d for panel 16. The absorbent 15 may be bonded to the lateral edges of the front and back sections of the backsheet. As shown in FIG. 2, nonwoven inner layer 18 covers absorbent layer 15 and its outer periphery may have its edges bonded or glued to the backsheet 11 as at 19 to completely encase the absorbent layer 15. The absorbent layer 15 with its encasing nonwoven layer 18 will traverse the front section 12, crotch section 14, and back section of 13 of the backsheet 11. The outline 15a of the absorbent layer 15 on the front section 12 can be seen in FIG. 1.

The elastic side panels 16 and 17 in combination with crotch section 14 of the backsheet 11 define leg openings 21 and 22 as illustrated in FIG. 1. Backsheet 11 may have an hourglass shape to better conform to the body of the diaper wearer.

Optionally, the diaper may include front and back elastic bands 24 and 25 in the waist area and secured to the backsheet 11; and elastic leg bands 27 and 28 secured to backsheet 11 and surrounding a lower portion of each leg opening 21 and 22. The waist bands 24 and 25 in combination with upper edge portions 29 and 30 of side panels 16 and 17 define a circumferential diaper waist 26.

The backsheet, absorbent, and elastic bands may be constructed according to techniques well known in the art and described at length in the literature. For example, the backsheet may be made of a polyolefin film such as polypropylene or may be a composite of a polyolefin film and a nonwoven cover bonded thereto. The absorbent may be made of cellulosic material with or without a gelling agent. The bands may be made of elastic strips or elastomerics as described in the aforementioned U.S. Pat. Nos. 4,720,415 or 5,226,992.

The novelty of the form fitting diaper constructed according to the present invention resides in the composition of the elastic side panels 16 and 17.

Figure 4:
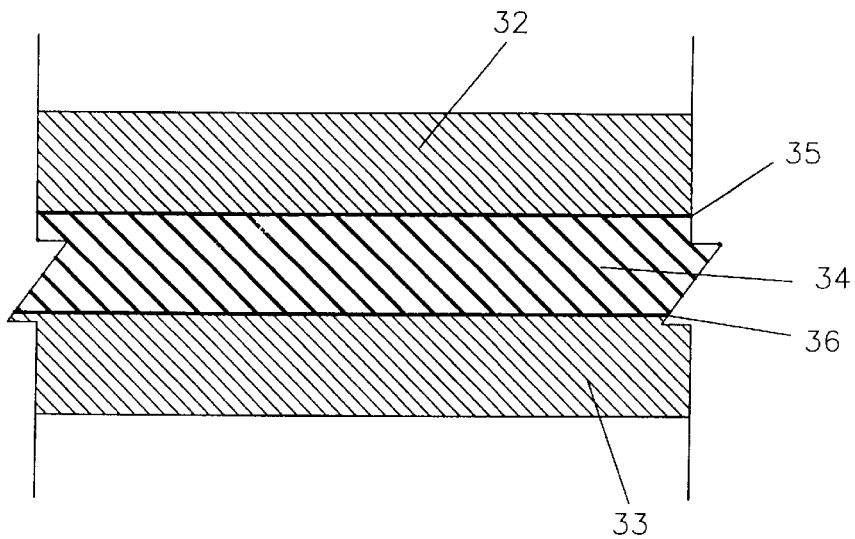
FIG. 4 is a longitudinal sectional view of an elastic composite useful in the diaper of the present invention.

As shown in FIG. 4, the composite 31 of the present invention preferably comprises three layers 32, 33, and 34 bonded together by adhesive layers 35 and 36 at the layer interfaces. As indi-cated above, in some uses the composite may comprise only one of the nonwoven layers 32 or 33.

Layer 34 is an elastomer and layers 32 and 33 are stretchable or elastic nonwovens made from nonelastic thermoplastic fibers. Elastomeric layer 34 adds strength to the side panels which may be stretched to a large degree when the diaper is put on or taken off. The nonwoven layers 32 and 33 provide unidirectional elasticity, softness and breatheability to the diaper for comfort.

Elastomeric Layer

The layer of elastomer 34 may be made from any elastomeric web or sheet, but is preferably made from extruded film or meltblown web consisting of thermoplastic elastomers.

The extrusion of elastomers to form film and meltblown fabrics is well known in the industry. Thermoplastic elastomers (described above) preferably include the styrene based block copolymers incorporating butadiene or isoprene as the aliphatic chain segment, the Kraton styrene-butadiene® copolymers manufactured by Shell Chemical Company, polyether ester family of elastomers used in the manufacture of elastic meltblown fabrics marketed by Kimberly-Clark under the trademark Demique®, and the ethylene vinyl acetate and the ethylene methyl acrylate copolymers developed by Exxon Chemical Company. The thermoplastic elastomers are not limited to the polymers and copolymers described above, but may include any sheet form or web form of elastomeric material that can be bonded to the nonwoven web.

The elastomeric layer 34 itself may be a composite of one or more layers and may include additives such as polyolefins.

Many of the elastomers mentioned above and others including pressure sensitive elastomers are described in detail in U.S. Pat. No. 5,226,992, the disclosure of which is incorporated herein by reference.

Elastic Nonwoven Webs

The elastic nonwoven web (layers 32 and 33) useable in the present invention is made by a process known as "stretchable nonwovens" which is described in detail in U.S. Pat. No. 5,244,482 and referred to in the *Nonwovens World* article cited above. This process imparts unidirectional elasticity to nonwoven webs composed of nonelastic fibers or filaments.

Although the nonwoven web may be made by a variety of processes, including meltblowing, spunbond, thermally bonded staple fibers, spunlaced webs, and the like, the preferred nonwovens are meltblown and spunbond webs. The most preferred nonwovens are meltblown webs.

As described in detail in U.S. Pat. No. 5,244,482, the disclosure of which is incorporated herein by reference, the elastic nonwoven webs are made by stretching a nonwoven precursor web in one direction under heated conditions to cause the nonelastic fibers of the web to consolidate in the direction of stress. This causes a number of the fibers in the web to align in the direction of stress and other fibers disposed cross-wise thereof to resist the alignment or consolidation. The process temperature is slightly below the polymer melting point. Upon the release of the stress and cooling of the web, the web exhibits good elasticity transverse the direction of applied stress or draw (stretch). The web further exhibits substantially inelastic behavior in the direction of the draw. The unidirectional elasticity is mechanical (spring-like) in nature as opposed to being elastomeric. The controlled draw ratio under the thermal conditions ranges from about 1.05 to 4.0 (e.g. 5% to 300%, with the preferred being from 10% to 100%).

The important parameters of the precursor web and the process conditions, along with the unique properties of the web produced by the process, are described in detail below.

A nonelastomeric nonwoven precursor web is selected based on its dimensions, and its hot processing tensile properties (i.e., elongation-at-break). In general, the breaking draw ratio of the web during hot processing should be less than about 4.0 and greater than about 1.4 evaluated while hot drawing at a strain rate greater than 2500%/min and a temperature greater than the softening point but at least 10° F. less than the polymer melting temperature. The breaking draw ratio is an important indicator of precursor molecular orientation state for achieving sufficient stresses for cross-direction (CD) fiber buckling and bending, whereby there is a reduction of the pore size distribution of the web by the process described in U.S. Pat. No. 5,244,482. The room temperature elongation strain-at-break should be between 2 and 40%, preferably between 5 and 20% percent, based on test method ASTM D 1117.77 using the Instron tensile testing machine.

Compressive stresses which buckle and bend CD fibers are described mathematically by a sine function of the fiber tensile stress; and the angles involved become smaller as the machine direction (MD) draw ratio increases. Therefore, compressive stresses decrease sinusoidally with draw ratio. Elastomeric polymer webs cannot be used for the nonwoven layers in the present invention.

The precursor nonwoven web may be made from many of the thermoplastics capable of being meltblown, provided the polymer selected develops filaments of sufficiently high tensile processing modulus to permit the development of high lateral compression forces on the web. The thermoplastic resins useable in the production of nonwovens includes the nonelastomeric polyolefins including homo and copolymers of ethylene and propylene such as polyethylene, polypropylene including high density polyethylene, ethylene copolymers (including EVA and EMA copolymers with high tensile moduli), nylon, polyamides, polyesters, polystyrene, poly-4-methylenepentene-1, polymethylmethacrylate, polytrifluorochloroethylene, polyurethanes, polycarbonates, silicones, and polyphenylene sulfide.

The crystallinity of the precursor web preferably should be sufficiently high to provide a room temperature breaking elongation less than 40%. The precurser meltblown webs should break at a strain of less than 40% in accordance with ASTM test method D 5035-90. The crystallinity in the range of 30 to 70% is preferred. In general, the proper high modulus and state of molecular orientation of the precursor is best reflected by a maximum or breaking draw ratio of the web during post treating of less than about 4.0.

In the post treatment process, the thickness of the web should preferably be at least 2 mils and up to about 200 mils.

The width of the web, of course, can vary within wide limits, with 5 to 150 inches being preferred. The average fiber diameter of the precursor meltblown web will preferably range from 0.5 to 20 microns, with 0.5 to 10 microns being most preferred in order to provide the proper range of processing tensile stiffness for the web. The porosity of the precursor web will normally be in the range of 50 to 95%. Calendered precursor webs approach 50%.

Other properties of the web, which while not critical, are important and include a low occurrence of large shot or excessive ropiness.

Another important feature of the precursor web is that it includes at least some fiber-to-fiber bonding which is typical in meltblown webs. The bonding can be achieved by inherent fiber-to-fiber fusion, or by point bonding, calendering, or by fiber entanglement. The properties of the selected polymer can be controlled to a degree by controlling the conditions of the meltblowing process. Some of these control variables are disclosed under the experiments described in U.S. Pat. No. 5,244,482.

As indicated above, the primary purpose of the process of the present invention is to consolidate the web in the cross-direction to reduce the average pore size and the pore size distribution in the web. Consolidation of the web in the cross-direction is to be distinguished from consolidation resulting from calendering since consolidation to reduce thickness as in calendering flattens the fibers and closes flow channels, thus decreasing the permeability of the web to a greater extent compared to web draw consolidation.

The random nonwoven nature of low stretch meltblown webs with the attendant thermal bonding and/or filament entanglement enable the development of MD stresses to reorient fibers and create sufficient compressive stresses to laterally (CD) consolidate or squeeze them together thus reducing the size of voids therebetween during uniaxial drawing. This results in narrowing of the web width without disrupting the planar integrity of the web and produces a product of unique properties. During the post-drawing process, the modulus that is in effect while the filament segments are being drawn depends on processing time-temperature effects. Maximum consolidation in the CD is achieved at a trial and error modulus at which the compressive stresses overcome to the largest extent the critical buckling stresses for the population of CD segments in the web. The following table gives preferred operating parameters for manufacturing the elastic meltblown webs.

|  | Broad Range | Preferred Range | Best Mode |
| --- | --- | --- | --- |
| Draw Ratio | 1.05–4.00 | 1.10–2.00 | 1.2–1.80 |
| Temperature (°F.) (PP) | 165–350 | 250–350 | 275–300 |
| Crystallinity (%) | 30–95 | 30–80 | 35–60 |
| Thickness, (mils) | 2–200 | 2–100 | 3–20 |
| Avg. Fiber Dia. (microns) | 0.5–50 | .5–20 | .5–10 |
| Strain rate, (%/min) | 10–500 | 20–200 | 30–60 |
| Elastic Recovery (%) | 50–99 | 70–99 | 80–95 |

As mentioned above, details of the processing conditions and properties of the resulting web are found in the aforementioned U.S. Pat. No. 5,244,482. This process imparts unidirectional elasticity to a nonwoven web of inelastic fibers. This elasticity is mechanical (spring-like) in nature rather than rubber-like in nature. Thus the elastic nonwoven retains its physical cloth-like appearance and feel.

Nonwoven layers 32 and 33 may consist of a mixture of thermoplastics and may include additives such as absorbents, superabsorbents, surfactants, and dyes to improve certain properties of the nonwovens.

The elastic nonwoven web may itself consist of more than one layer as demonstrated in the aforementioned U.S. Pat. No. 5,244,482.

Method of Manufacture of the Elastic Composite

As previously mentioned, the composite 31 useful as side panels in the diaper illustrated in FIG. 1 comprises two layers 32 and 34 or 33, or three layers 32, 33, and 34 which are bonded together by any means including thermal bonding or by the application of chemical or adhesive layers 35 and 36 (see FIG. 4) at the interfaces. Other bonding techniques such as ultrasonic welding, hydro-entanglement, and the like, may also be used.

The thermal bonding can be achieved by techniques well known in the art wherein the two or three layers 32, 33, and 34 are passed through the nip of counter-rotating heated rollers with or without embossments to thermally bond or fuse the layers together.

In accordance with one aspect of the present invention, laminating the preferred three layers together to form the composite 31 may be by a process schematically illustrated in FIG. 3 and described below. (The two-layer embodiment may be similarly laminated using only one applicator.)

An elastomeric layer 34 is dispensed from a roll mounted on spindle 38; an elastic nonwoven web 32 is dispensed from a roll mounted on spindle 39; and a second elastic nonwoven web 33 is dispensed from a roll mounted on spindle 40.

A hot melt adhesive applicator 41 is disposed over one surface of web 32 and a hot melt adhesive applicator 42 is disposed over a top surface of layer 33. Applicators 41 and 42 discharge an adhesive spray 43 and 44 onto their respective underlying surfaces 32 and 33.

The three layers 32, 33, and 34 are fed into nip 46 of counterrotating rollers 47 and 48, with the elastomeric layer 34 being sandwiched between the flanking elastic nonwoven layers 32 and 33. The counterrotating rollers 47 and 48 compress the three layers 32, 33, and 34 together as they pass through the nip 46, and pressure bond them together to form composite 31.

Guide rollers 49 are used to tension and guide the respective layers 32, 33, and 34 in the process. The composite 31 is wound on spindle 50.

The layers 32, 33, and 34 are pulled through the nip by driven spindle 50 so that all three layers have the same line speed. Guide rollers 49 maintain very little tension on the layers to avoid stretching.

The rollers 47 and 48 may be smooth, embossed or coated, and may be heated or unheated. The pressure at the nip 46 may vary within a wide range, depending on the type of bonding. One of rollers 47 and 48 may be embossed as in a diamond pattern to create compressive regions on the layers passing therethrough. The embossment normally will comprise between 1 to 19% of the roll surface area.

The line speed of the layers through the nip will typically be 50 to 350 feet per minute, preferably 200 to 300 feet per minute.

The dispensers for dispensing the hot melt adhesive may be commercial spray nozzle applicators, commercial bead applicators, or commercial meltblown dispensers manufactured by J&M Laboratories, Inc. All that is necessary is that the bonding means provide at least two transversely spaced bond regions along the layers being bonded together. Preferably, the bond regions are in the form of a meltblown or spray film of adhesive material covering the mating surface to be bonded, producing a three-layer composite which behaves as a single fabric.

Any of the commercial hot melt adhesives capable of bonding the layers may be used. The preferred hot melt adhesives are the SIS and SBS block copolymer based adhesives. These adhesives contain the block copolymer, tackifier, and oil in various ratios, typically 80–85 wt %, 5–10 wt %, and 5–15 wt %, respectively.

The dimensions and properties of the composite 31, of course, will vary within wide limits depending upon the materials used in each layer, the bonding process, the amount of materials in each layer, additives, and the intended application, etc. However, by way of example, the following dimensions and properties are representative:

|  | Basis | | Avg. Fiber Diam. (microns) | |
| --- | --- | --- | --- | --- |
|  | Thickness (mils) | Weight (Oz./yd$^2$) | Broad Range | Preferred Range |
| Thermoplastic Elastomer (layer 34): Film | 0.5–3.0 | 0.5–2.0 | N/A | N/A |
| Elastic Nonwoven (layers 32 and/or 33): | | | | |
| Meltblown | 3–20 | 0.5–2.0 | .5–15 | .5–10 |
| Spunbond | 3–20 | 0.5–2.0 | 15–50 | 20–30 |

The unidirectional elasticity of the composite 31 may be described with reference to FIG. 5 wherein composite 31 is illustrated as having a length L and an unstretched normal width W. As has been described above, composite 31 comprises nonwoven web layers 32 and 33 with elastomeric layer 34 bonded therebetween. The composite preferably exhibits properties of a single fabric in stretching, contracting, and handling. Elastic nonwoven webs 32 and 33 were each made by being drawn in the direction illustrated by arrow 51 by the heat drawing process described above with reference to U.S. Pat. No. 5,244,482, so that the webs each exhibit unidirectional elasticity, or stretchability, in a direction at right angles to arrow 51. Arrow 51, therefore, represents the machine direction (MD) of the heat drawing process. Nonwoven webs 32 and 33, and thus composite 31, will have unidirectional elasticity in the direction of arrow 52, and be substantially inelastic in the cross-direction (CD) represented by the direction of arrow 51. Thus in relation to the diaper illustrated in FIG. 1, arrow 52 would correspond to the circumferential direction of the diaper waist, and arrow 51 would be perpendicular thereto. Elastomeric layer 34 exhibits elasticity in substantially all directions in the plane of FIG. 5.

Figure 5:
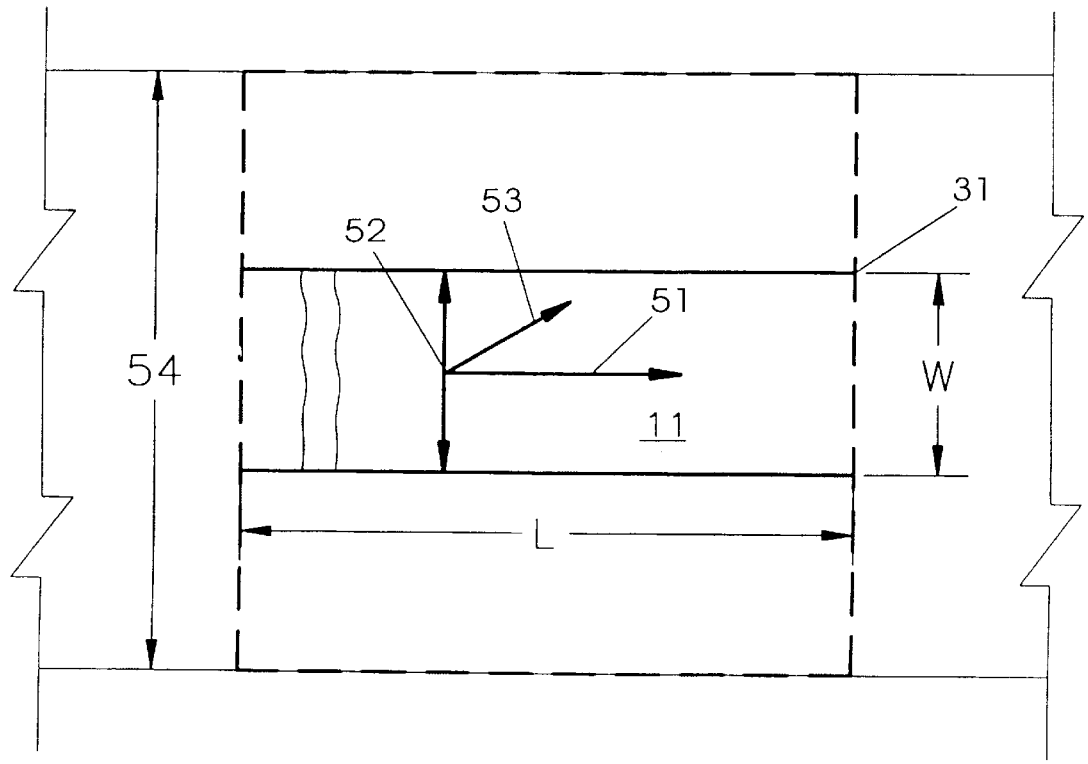
FIG. 5 is a top plan view of the composite shown in FIG. 4 illustrating its unidirectional elasticity.

Also illustrated in FIG. 5 is the situation where a force is applied in a direction between arrows 51 and 52, as represented by arrow 53. This force will have a CD component parallel to arrow 52, and a MD component in the direction of arrow 51. Due to the unidirectional elastic properties of composite 31, the composite will stretch in the direction of arrow 52 in proportion to the CD component only, and be substantially inelastic to the MD component in the direction of arrow 51. The elastic composite 31 is stretchable in a direction indicated by arrow 52 to about 400%, preferably 300%, and most preferably 200%, of its original width with the elastic elongation indicated by arrow 54. The recovery from the elongation should be to the composite's original width or 5% to 10% of the original width. For elongations of 100% (e.g. the elongation 54 equals two times W) the recovery should be within 10% of the original width W, preferably within 5%, after several loading and unloading cycles.

One of the defining characteristics of the composite 31 useable in the diaper of the present invention is that the elastic nonwoven layers 32 and 33 permit the thermoplastic elastomer layer 34 to stretch in a direction transverse the length, indicated by arrow 52, but prevents the elastomer from stretching in the MD, indicated by arrow 51. This, of course, assumes that the elastic nonwoven web had been made by heat stretching in the MD. As has been described, the unidirectional elasticity of the composite 31 when used as side panels 16 and 17 facilitates the pull-up of diaper 10 by providing elasticity in the circumferential waist direction and inelasticity in the direction of the pull-up.

It will be appreciated that it is possible to use elastic nonwoven layers 32 and 33 that have been drawn (under thermal conditions) in the CD (arrow 52) whereby the elasticity of composite 31 is in the MD (arrow 51).

A significant difference between the composite 31 and that described in U.S. Pat. No. 5,226,992 is that the nonwoven web, because of its elastic properties, assists in the recovery of the composite to its original or near its original unstretched dimension; whereas, the necked-bonded material of U.S. Pat. No. 5,226,992 does not itself possess elasticity, but merely permits the web to be stretched in a direction parallel to the direction of necking.

EXAMPLES

A three layer composite 31 was made and tested. The composite had the following layers:

| | |
| --- | --- |
| layer 32 | Stretchable polyester nonwoven (carded) |
| | Thickness: 5 mil |
| | Basis Weight: 0.6 oz/yd$^2$ |
| | Average Fiber Size: 30 microns |
| layer 34: | Elastomeric Film: Styrene triblock copolymer |
| | Thickness: 1.0 mil |
| layer 33: | Polypropylene Spunbond |
| | MFR: 35 |
| | Thickness: 4 mils |
| | Basis Weight: 0.6 oz/yd$^2$ |
| | Average Fiber Size: 20 microns |
| Adhesive: | Hot Melt Adhesive HM-1295 marketed by H. B. Fuller |
| Adhesive Amount: | 5 Grams per square meter |

Figure 3:
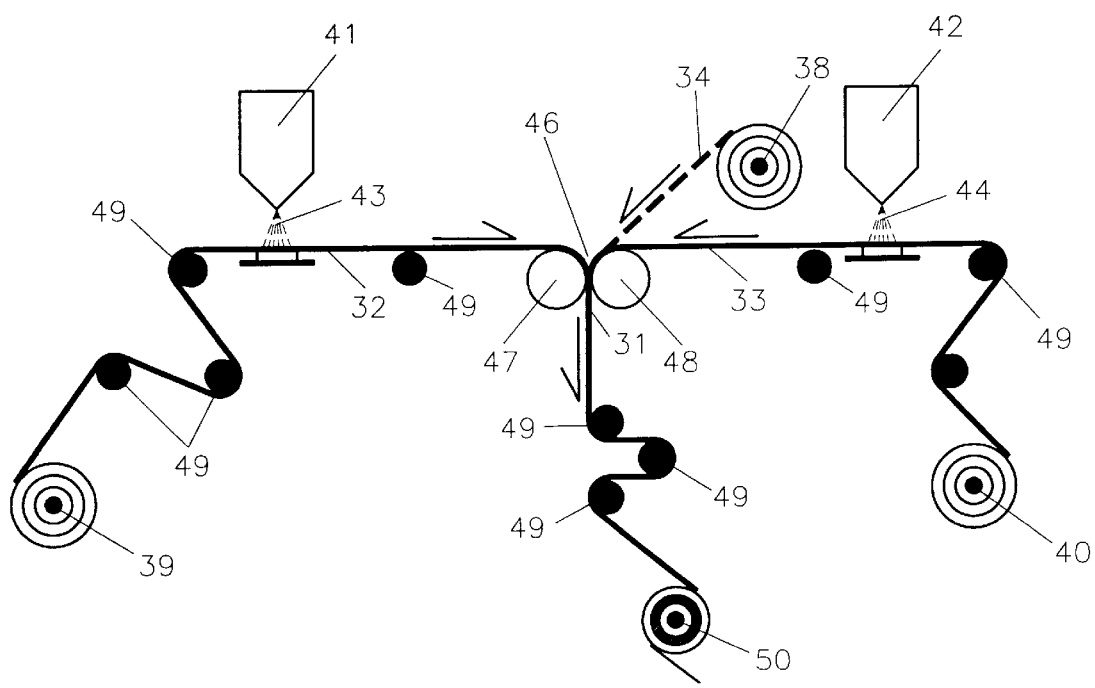
FIG. 3 is a schematic illustrating the laminating apparatus for forming an elastic composite useful in the diaper of the present invention.

The composite was made using an apparatus similar to FIG. 3 wherein the counterrotating rollers 47 and 48 were smooth rollers. Layer 34 is elastic in the machine direction (direction of travel) of the apparatus of FIG. 3, while web layers 32 and 33 may be elastic or inelastic in the machine direction depending on the unidirectional orientation of the layers when they are manufactured, as has been discussed in relation to FIG. 5. For the web shown in FIG. 5, layers 32 and 33 will be inelastic in the machine direction (arrow 51) and elastic in the transverse direction (arrow 52). In either case, drive spindle 50 imparts very little tension on the layers of the composite so there is minimal or no stretching.

In the test results described below, the thermoplastic elastomer web 34 was fed sandwiched between the elastic nonwoven webs 32 and 33 into the nip 46 of the counterrotating rollers operating at a pressure of 50 pounds per linear inch and a temperature of approximately 72° F. (ambient). The line speed was 300 feet per minute. Note that the line speed of the composite exiting the nip was the same as the line speed of the layers fed into the nip. The composite was 12 mils thick and 12 inches wide. Samples of the composite were cut from the roll stock and tested. The tests are described as follows.

Figure 6:
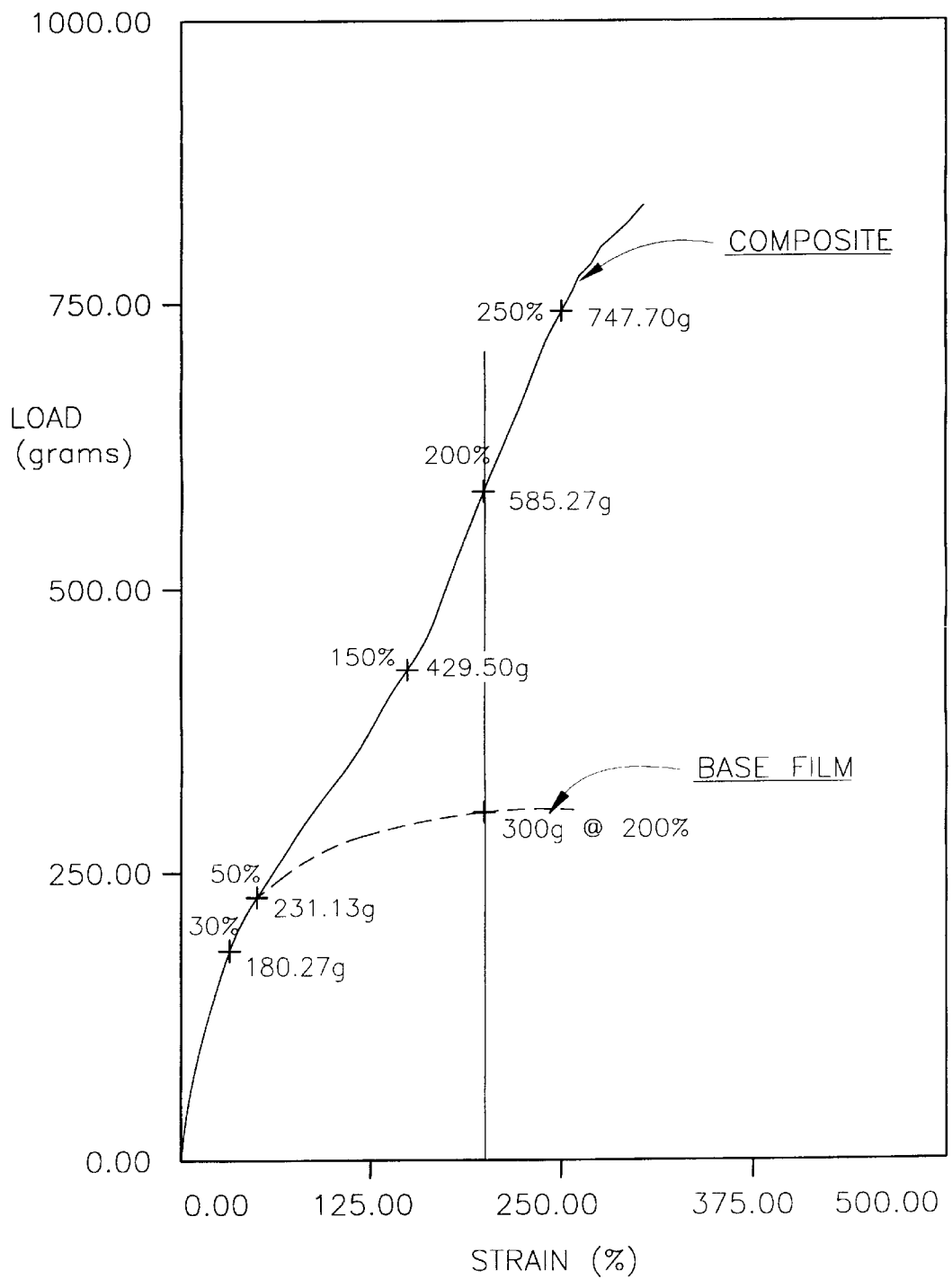
FIG. 6 is a stress/strain diagram illustrating the elasticity of the composite used in the diapers of the present invention.

Stress/strain tests were carried out on samples of the composite and the base elastomeric film (layer 34) alone. The stress vs. strain data (FIG. 6) reveal that the composite exhibits properties similar to the base film up to strains of about 50%. At strains above 50%, the composite behavior is different than that of the base film. The composite has nearly linear behavior up to and beyond a strain of 250%, while the base film alone begins to exhibit nonlinear behavior above 50%. Linear stress/strain behavior is typical of springs and/or spring-like materials.

The above tests demonstrate that the composite 31 has excellent elasticity closely tracking that of the elastomer at low strain levels, remaining spring-like at higher strain levels, while composite 31 also exhibits the hand and aesthetics of the nonwoven material. The composite of the present invention can be tailored to meet a variety of needs which would combine the barrier properties of film or other meltblown elastomeric, and the protective covering and soft hand of the nonwoven fabrics.

Fabrication of the Form Fitting Diaper

The composite 31 is used as diaper side panels 16 and 17 (see FIG. 1) in the manner described above. The composite 31 is positioned to be bonded to the front 12 and back 13 of the backsheet 11 so that stretchability or elasticity is in a circumferential direction (indicated by arrow 56) of FIG. 1, but not in the vertical direction. This is important because the wearer generally grips the side panels and pulls upwardly to properly locate the diaper on the body. Elasticity in the vertical direction (as viewed in FIG. 1) of the side panels 16 and 17 would make it difficult to pull the diaper up.

The side panels may be bonded directly to the backsheet 11 at overlapped 20 edges, illustrated in FIG. 2. FIG. 2 illustrates bonding of the composite 31 with the crotch section of backsheet 11 at overlaps 20. A similar overlap bonding may be used to bond the composite to the front 12 and back 13 sections of the backsheet by overlapping the composite with the lateral edges of the front and back sections as illustrated by 20a and 20b for panel 17, and 20c and 20d for panel 16. Alternatively, a nonwoven web or sheet may be bonded to the backsheet 11 and that web or sheet bonded to the side panels along edge seams.

Optionally, side panels 16 and/or 17 may comprise a front panel and a back panel which are joined along a seam intermediate the backsheet front 12 and back 13. With reference to FIG. 1, side panel 17 comprises front panel 17a bonded to a lateral edge of backsheet front section 12 at 20a, and back panel 17b bonded to backsheet back section 13 at 20b. Front panel 17a and back panel 17b are bonded together along seam 57b intermediate front 12 and back 13. Seam 57b runs substantially from waist 26 to leg opening 22. The seam may be formed using a variety of well known bonding techniques such as adhesives or heated pressure bonding. The combination side panel 17 comprising panels 17a and 17b exhibits the unidirectional elasticity and fabric-like properties heretofore discussed in detail. Side panel 16 may likewise be a combination of front panel 16a and back panel 16b bonded to the backsheet at 20c and 20d, and further bonded along seam 57a. Seams 57a and 57b may be bonded in a fashion whereby the seams may be easily ripped apart to quickly remove the diaper in the event the diaper is to be disposed of.

Although the present invention has been described with specific reference to diapers, it is to be recognized that the invention can be used in any garment with stretchability.

For example, the composite 31 may be used in the waist 26 of the diaper 10 to impart stretchability thereto. Briefly, a strip of the composite 31 will be stretched, and in the stretched condition bonded to the diaper backsheet in the waist area at spaced locations along the composite strip length. Upon release, the composite will contract with the diaper backsheet forming ruffles along the composite strip.

What is claimed is:

1. A form fitting diaper for a human body, which comprises:
   (a) a backsheet having
      (i) a front section having spaced apart lateral edges,
      (ii) a back section having spaced apart lateral edges, and
      (iii) a crotch section interconnecting the front and back sections;
   (b) a nonwoven inner layer having its outer periphery bonded to the backsheet;
   (c) an absorbent layer positioned between the backsheet and the nonwoven inner layer;
   (d) a first side panel interconnecting one lateral edge of the front of the backsheet section to one lateral edge of the back section of the backsheet; and
   (e) a second side panel interconnecting the other lateral edge of the front section of the backsheet with the other lateral edge of the back section of the backsheet, the side panels and the front and back sections of the backsheet defining a circumferentially continuous waist adapted to fit around the body, each side panel being composed of a composite comprising
      (i) a first layer of a stretchable, elastic nonwoven composed of nonelastic fibers;
      (ii) a second layer of a stretchable elastic nonwoven composed of nonelastic fibers, and
      (iii) an elastomeric layer positioned between the first and second layers and having one surface bonded to the first layer and a second surface bonded to the second layer; whereby the composite is stretchable without requiring ruffles in any of the layers.

2. The form fitting diaper of claim 1 wherein the first and second layers of the elastic nonwovens exhibit elasticity in the circumferential direction of the waist and are substantially nonelastic in a direction perpendicular thereto.

3. The form fitting diaper of claim 2 wherein the nonelastic fibers of the first and second layers of the side panel nonwovens are spunbond or meltblown fibers having a fiber diameter of between 0.5 and 50 microns.

4. The form fitting diaper of claim 3 wherein the nonwovens are meltblown fibers having an average fiber diameter of between 0.5 and 15 microns.

5. The form fitting diaper of claim 1 wherein the layers of each side panel are bonded together by a layer of hot melt adhesives so that the composite behaves as a single fabric.

6. The form fitting diaper of claim 1 wherein the elastomeric layer is a film made of a thermoplastic elastomer.

7. The form fitting diaper of claim 6, wherein the elastomeric film is a thermoplastic elastomer selected from the styrene triblock copolymers.

8. The form fitting diaper of claim 1 wherein the first and second layers comprise thermoplastic fibers.

9. The form fitting diaper of claim 8 wherein the nonwoven layers comprise polyolefin fibers.

10. The form fitting diaper of claim 9 wherein the polyolefins are selected from the group consisting of homo and copolymers of propylene and ethylene.

11. The form fitting diaper of claim 1 wherein the first and second nonwoven layers of the side panels are made of fibers of different compositions, respectively.

12. The form fitting diaper of claim 1 wherein the first and second nonwoven layers are of the same composition.

13. The form fitting diaper of claim 1 wherein the composite exhibits substantially unidirectional elasticity of at least 100% with at least 90% recovery.

* * * * *